United States Patent [19]
Blanchard et al.

[11] Patent Number: 5,399,708
[45] Date of Patent: Mar. 21, 1995

[54] PYRAZOLIDIN-3-ONE DERIVATIVES

[75] Inventors: William B. Blanchard, Indianapolis; Thomas C. Britton, Carmel; David L. Varie, Indianapolis, all of Ind.

[73] Assignee: Eli Lilly and Company, Indianapolis, Ind.

[21] Appl. No.: 153,843

[22] Filed: Nov. 12, 1993

[51] Int. Cl.$^6$ ............................................ C07D 231/08
[52] U.S. Cl. ............................ 548/366.4; 548/364.1
[58] Field of Search ...................... 548/366.4, 364.1

[56] References Cited

FOREIGN PATENT DOCUMENTS 467614  1/1992  European Pat. Off. .
159850  1/1964  U.S.S.R. .

OTHER PUBLICATIONS

F. Zymalkowski et al., *Archiv. der Pharmazie*, 302, Band, Heft 4, 272–284 (1969).
R. M. Claramunt et al., *Org. Prep. Proced. Int.*, 23(3), 273–320 (1991).
S. T. Perri et al., *J. Org. Chem.*, 55, 6037–6047 (1990).
B. P. Czech et al., *J. Org. Chem.*, 49, 4076–4078 (1984).
C. Sabaté-Alduy et al., *Bulletin de la Société Chimique de France*, No. 9–10, 1942–1948 (1974).
E. F. V. Scriven, *Chem. Soc. Rev.*, 12, 129–161 (1983).

*Primary Examiner*—Robert W. Ramsuer
*Attorney, Agent, or Firm*—MaCharri R. Vorndran-Jones

[57] ABSTRACT

The present invention provides an enantiomerically selective process and intermediates for preparing certain 4,5-disubstituted pyrazolidinones and intermediates which are useful for treating diseases of the central nervous system.

2 Claims, No Drawings

PYRAZOLIDIN-3-ONE DERIVATIVES

FIELD OF THE INVENTION

This invention provides an enantiomerically selective process for preparing certain 4,5-disubstituted pyrazolidinones and intermediates.

BACKGROUND OF THE INVENTION

Cholecystokinin (CCK) is a neuropeptide found in both gastrointestinal tissue and the tissues of the central nervous system. Compounds which are CCK and gastrin antagonists are useful in the treatment and prevention of CCK and gastrin-related disorders of the gastrointestinal, central nervous, and appetite regulatory systems of warm-blooded vertebrates. One class of compounds exhibiting the desired CCK receptor binding properties are compounds of the formula 1.

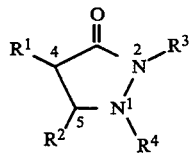

wherein $R^1$ and $R^2$ are independently hydrogen, $C_1$-$C_6$ alkyl, phenyl, benzyl, naphthyl, pyridyl or substituted phenyl having 1, 2, or 3 substituents selected from the group consisting of $C_1$-$C_6$ alkyl, $C_1$-$C_6$ alkoxy, $C_1$-$C_6$ alkylthio, chloro, fluoro, trifluoromethyl, phenyl, phenoxy, phenyl($C_1$-$C_4$ alkyl), phenyl($C_1$-$C_4$ alkoxy), cyano, carbamyl, methylenedioxy, $C_3$-$C_6$ alkene, amino, —NH($C_1$-$C_4$ alkyl or benzyl), and N($C_1$-$C_4$ alkyl ) 2;

$R^3$ is hydrogen, $C_1$-$C_6$ alkyl, carboxymethyl, $C_1$-$C_4$ alkoxycarbonylmethyl or a group of the formula

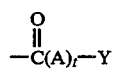

wherein t is 1 or 0; A is —$CH_2$—, —O—, —NH— or —N(-$C_1$-$C_6$ alkyl)—; and Y is phenyl or substituted phenyl as defined above;

$R^4$ is hydrogen or a group of the formula

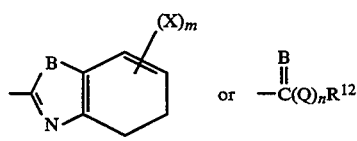

wherein

B is O or S; X is selected from the phenyl substituents defined above; m is 0, 1 or 2; n is 0 or 1; Q is —NH—, —N($C_1$-$C_6$ alkyl)—, —S—, or —O—; and $R^{12}$ is a group of the formula —[CH($R^{10}$)]$_q$—($CH_2$)$_r$—$R^{11}$ wherein $R^{10}$ is hydrogen or $C_1$-$C_6$ alkyl; q is 0 or 1; r is 0, 1 or 2; and $R^{11}$ is hydrogen, $C_1$-$C_8$ alkyl, $C_3$-$C_8$ cycloalkyl, pentafluorophenyl, pyridyl, tetrahydronaphthyl, indolyl, quinolinyl, phenyl, naphthyl, or phenyl or naphthyl substituted with 1, 2, or 3 substituents as defined above for phenyl; or the group —(Q)$_n$$R^{12}$ is 2-tetrahydroisoquinolinyl; and the pharmaceutically acceptable salts thereof.

Compounds of Formula 1 are described in published European patent application No. 91306374.9 (publication No. 0467 614 A1). The artisan will recognize that published European patents are readily available to the artisan in the United States. European patent applications are published in English so that the American artisan can easily read the publication.

The (+)-4(S),5(R)-enantiomer of certain trans isomers of compounds of formula 1 (i.e. (+)-1a infra.) have proven to be potent and selective antagonists of the CCK-B receptor subtype.

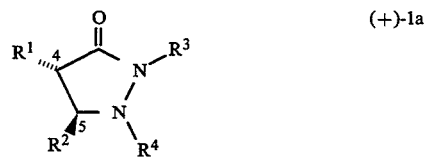

The antipodal (—)-4(R),5(S)-enantiomers of Formula 1 (i.e. (—)-1a infra. ) are potent and selective antagonists of the CCK-A receptor.

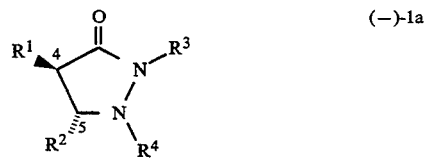

Small quantities of these materials have been isolated in enantiomerically pure form by high performance liquid chromatograpic resolution of diastereomeric derivatives of a racemic pyrazolidinone precursor. However, such methods have proven to be intractable for the generation of more than milligram quantities of pure enantiomers.

No general strategies have been reported or suggested in the literature for the enantioselective synthesis of compounds of formula 1. Known strategies for the synthesis of racemic variants of such compounds do not provide for the control of absolute stereochemistry at C-4 and C-5. This invention provides a process for the enantioselective synthesis of either (+)-1a or (—)-1a in a high degree of enantiomeric purity. Futhermore this invention provides new chemical compositions which are useful and necessary for the process claimed herein.

SUMMARY OF THE INVENTION

This invention provides a method for using a compound of Formula 2

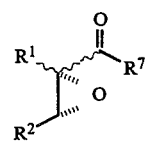

wherein $R^1$ and $R^2$ are independently hydrogen, $C_1$-$C_6$ alkyl, phenyl, benzyl, naphthyl, pyridyl or substituted phenyl having 1, 2, or 3 substituents selected from the group consisting of $C_1$-$C_6$ alkyl, $C_1$-$C_6$ alkoxy, $C1$-$C6$ alkylthio, chloro, fluoro, trifluoromethyl, phenyl, phenoxy, phenyl ($C_1$-$C_4$ alkyl) , phenyl ($C_1$-$C_4$ alkoxy) , cyano, carbamyl, methylenedioxy, $C_3$-$C_6$ alkene, amino, —NH($C_1$-$C_4$ alkyl or benzyl ) , and N($C_1$-$C_4$ alkyl)$_2$;

$R^7$ is $OR^8$ or $N(R^9)_2$; $R^8$ is hydrogen, phenyl, or $C_1-C_6$ alkyl; $R^9$ is independently hydrogen, $C_1-C_6$ alkyl, or $NH_2$;

to prepare a compound of Formula (+)-1a

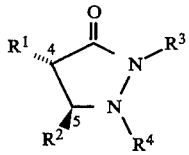

(+)-1a $R^3$ is hydrogen, $C_1-C_6$ alkyl, carboxymethyl, $C_1-C_4$ alkoxycarbonylmethyl or a group of the formula,

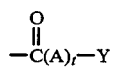

wherein
t is 1 or 0; A is $-CH_2-$, $-O-$, $-NH-$ or $-N(-C_1-C_6$ alkyl$)-$; and Y is phenyl or substituted phenyl as defined above;

$R^4$ is hydrogen or a group of the formula

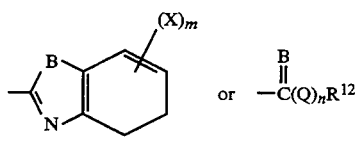

B is O or S; X is selected from the phenyl substituents defined above; m is 0, 1 or 2; n is 0 or 1; Q is $-NH-$, $-N(C_1-C_6$ alkyl$)-$, $-S-$, or $-O-$; and $R^{12}$ is a group of the formula $-[CH(R^{10})]_q-(CH_2)_r-R^{11}$ wherein $R^{10}$ is hydrogen or $C_1-C_6$ alkyl; q is 0 or 1; r is 0, 1 or 2; and $R^{11}$ is hydrogen, $C_1-C_8$ alkyl, $C_3-C_8$ cycloalkyl, pentafluorophenyl, pyridyl, tetrahydronaphthyl, indolyl, quinolinyl, phenyl, naphthyl, or phenyl or naphthyl substituted with 1, 2, or 3 substituents as defined above for phenyl; or the group $-(Q)_n R^{12}$ is 2-tetrahydroisoquinolinyl; and the pharmaceutically acceptable salts thereof;

comprising:
1) contacting a compound of Formula 2 supra with hydrazine to form a compound of Formula 4;

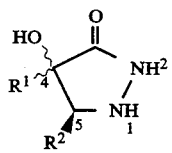

4 wherein $R^1$ and $R^2$ are defined supra.;

2) contacting the product of step 1 (4) with about 2 equivalents of di-tert-butyl dicarbonate and an acyl transfer catalyst to generate 6a;

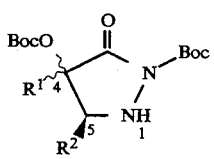

6a wherein $R^1$ and $R^2$ are defined supra.;

3) selective reductive cleavage of a compound of Formula 6a to generate 7

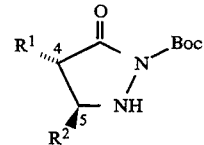

7 wherein $R^1$ and $R^2$ are as defined supra;

4) contacting the product of step 3 (7) with an acid to generate 8

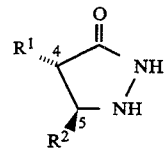

8 wherein $R^1$ and $R^2$ are as defined supra.;

5) acylating or alkylating the product of step 4 (8) to form a compound of Formula (+)-1a supra.

Also provided is a method for using a compound of the Formula 6

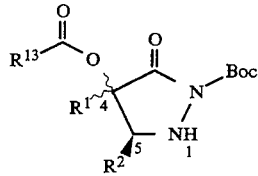

6 wherein
$R^{13}$ is $C_1-C_6$ alkyl, aryl, $CF_3$, or $OR^{14}$;
$R^{14}$ is $C_1-C_6$ alkyl or aryl;
$R^1$, $R^2$ are defined supra; to prepare a compound of Formula (+)-1a (described supra); comprising
1) selectively reducing a compound of Formula 6 to form a compound of Formula 7 supra;
2) contacting the product of step 1 (7) with an acid to generate a compound of Formula 8 (supra); and
3) alkylating or acylating the product of step 2 (8) to form compounds of Formula (+)-1a supra.

Additionally, there is provided a method for preparing a compound of Formula 6a (supra); comprising contacting a compound of Formula 4 (defined supra) with about two equivalents of di-tert-butyl dicarbonate ($Boc_2O$) and an acyl transfer catalyst.

Finally, there is provided a method for preparing a compound of Formula 8 (supra); comprising contacting a compound of Formula 6 (supra) with palladium, $H_2$, and a tertiary amine; and contacting the product of the hydrogenation step with an acid.

The compounds of Formulae 3, 4a, 5, 6, 6a, and 7 are new chemical entities. These new chemical entities are useful intermediates for the preparation of compounds of Formula (+)-1a.

Compounds of Formula 3 have the following structure:

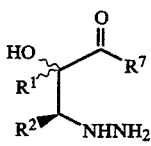

wherein $R^1$, $R^2$, and $R^7$ are defined supra.

Compounds of Formula 4a have the following structure:

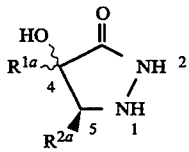

wherein $R^{1a}$ and $R^{2a}$ are independently hydrogen, $C_1-C_6$ alkyl, pheny, benzyl, naphthyl, pyridyl or substituted phenyl having 1, 2, or 3 substituents selected from the group consisting of $C_1-C_6$ alkyl, $C_1-C_6$ alkoxy, $C_1-C_6$ alkylthio, chloro, fluoro, trifluoromethyl, phenyl, phenoxy, phenyl($C_1-C_4$ alkyl), phenyl($C_1-C_4$ alkoxy), cyano, carbamyl, methylenedioxy, $C_3-C_6$ alkene, amino, —NH($C_1-C_4$ alkyl or benzyl), and N($C_1-C_4$ alkyl)$_2$; provided that when $R^{2a}$ is phenyl or substituted phenyl $R^{1a}$ may not be hydrogen.

Compounds of Formula 5 have the following structure:

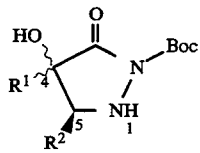

wherein $R^1$, $R^2$, and Boc are as defined supra.

DETAILED DESCRIPTION OF THE INVENTION

As used herein the term "$C_1-C_6$ alkyl" includes both straight and branched chain alkyl and cycloalkyl and includes methyl, ethyl, propyl, cyctopropyl, isopropyl, butyl, methylcyclopropyl, cyclobutyl, isobutyl, t-butyl, pentyl, cyclopentyl, neopentyl, hexyl, cyclohexyl, 2-methylpentyl and the like. In the phrases "$C_1-C_6$ alkoxy" and "$C_1-C_6$ alkylthio" substituents, the alkyl portion of the $C_1-C_6$ alkyl is as defined above. The term "halo" refers to fluoro, or chloro.

The term "alkene" refers to a carbon chain having one double bond at any position on the carbon chain. The terms "phenyl ($C_1-C_4$ alkyl)" and "phenyl ($C_1-C_4$ alkoxy)" refer to phenyl groups having alkyl or alkoxy substituents respectively.

The term "aryl" refers to phenyl, substituted phenyl, naphthyl, and substituted naphthyl. Preferably, aryl refers to phenyl or naphthyl.

The term "tertiary amine" refers to compounds of the formula

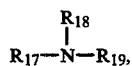

wherein $R_{17}$, $R_{18}$, and $R_{19}$ are independently selected from the group consisting of hydrogen, $C_1-C_8$ alkyl, aryl, $C_5-C_8$ cycloalkyl, $C_7-C_{16}$ arylalkyl, $C_5-C_8$ cycloalkyl-($C_1-C_3$)alkyl, and ($C_1-C_3$)alkyl, or $R_{17}$ and $R_{18}$ together with the nitrogen form a five to eight member saturated heterocyclic ring which may be substituted with up to 3 $C_1-C_5$ alkyl substituents; or $R_{17}$ and $R_{18}$ together may form a five to eight member unsaturated heterocyclic ring with the nitrogen. Preferred tertiary amines are those wherein $R_{17}$, $R_{18}$, and $R_{19}$ are independently selected from the group consisting of hydrogen, and $C_1-C_8$ alkyl, or $R_{17}$ and $R_{18}$ together form a five to eight member saturated heterocyclic ring with the nitrogen. Examples of preferred tertiary amines include triethylamine, diisopropylethylamine, pyridine, 2,4,6-trimethylpyridine, 2,6-dimethylpyridine, 2,6-di-t-butylpyridine, 2,6-di-t-butyl-4-methylpyridine, 4-pyrrolidinophyrdine, 4-dimethylaminopyridine, and N-methylmorpholine. Most preferred tertiary amines are those wherein $R_{17}$, $R_{18}$, and $R_{19}$ are $C_1-C_8$ alkyl; for example, triethylamine, diethylmethylamine, and trimethylamine.

The term "protic solvent" refers to a solvent containing hydrogen that is attached to oxygen, and hence is appreciably acidic. Common protic solvents include such solvents as water, methanol, ethanol, 2-propanol, and 1-butanol.

The term "inert atmosphere" refers to reaction conditions in which the mixture is covered with a layer of inert gas such as nitrogen or argon.

The term "hydrazine" includes anhydrous hydrazine, hydrazine hydrates, and stable hydrazine salts. Preferred hydrazine salts are acetate, dihydrochloride, monohydrochloride, and sulfate. More preferrably, hydrazine refers to anhydrous hydrazine or hydrazine hydrate.

The phrase "aqueous solvent" refers to a solvent which is from about 95% to about 100% water. The most preferred aqueous solvent is about 100% water.

The phrase "about 2 equivalents of di-tert-butyl dicarbonate" refers to using from about 1.75 equivalents to about 2.50 equivalents of di-tert-butyl dicarbonate. More preferredly the phrase refers to using from about 2.0 to about 2.3 equivalents.

Preferredly, "acid" refers to a protic acid. The more preferred acids are anhydrous. Most preferred acids include hydrochloric, hydrobromic, hydroiodic, trifluoroacetic, and sulfuric. Especially preferred acids include hydrochloric, and trifluoroacetic acid.

The phrase "selective reductive cleavage" includes dissolving metal reductions, electrochemical reductions, and palladium catalyzed reductive cleavage. Dissolving metal reductions may be completed using alkali, or alkaline earth metals in ammonia, dimethyl-2-imidazolidinone (DMI) or dimethyl-3,4,5,6-tetrahydro-2-(1H)-pyrimidinone (DMPU). See, Birch et al. Adv. Org. Chem., 8, 1-65 (1972). Preferred dissolving metal reductions are completed using lithium, sodium, or calcium. Most preferredly, the term "selective reductive cleavage" refers to palladium catalyzed reductive cleavage as described in greater detail infra.

The term "acyl transfer catalyst" refers to 4-di($C_1-C_6$)alkylaminopyridines. The term is intended to embrace 4-di($C_1-C_6$)alkylaminopyridines which have properties as acyl transfer catalysts. Preferred acyl transfer catalysts include but are not limited to DMAP, 4-(4-methylpiperidino)pyridine and 4-pyrolidinopyridine as described by Chem. Soc. Rev., 12, 129 (1983). The most preferred acyl transfer catalyst is DMAP.

The term "contacting" refers to the process of bringing the named compound into apposition with the mixture or isolated product from the previous step of the process, unless indicated contra. For example, the phrase "contacting X1 with Y1" refers to apposing the named compounds X1 and Y1. The term "Contacting" indicates that a named compound may be added to the other; the two compounds may be contacted simultaneously; or a product, compound, or mixture may be added to the named compound. "Contacting" may occur with agitation. The "contacted" substances may or may not react with one another.

Thus, the phrase "contacting with an acid" refers to the process of apposing an acid with the mixture or the process of contacting the isolated product with an acid. The term "acid" is as defined supra.

Abbreviations used herein have their accepted meaning, unless stated otherwise. For example, "Me" refers to methyl, "Et" refers to ethyl, "Bu" refers to butyl, "t-Bu" and "t-butyl" refers to tertiary butyl, and "Ph" refers to phenyl. As used herein "Boc₂O" refers to di-tert-butyl dicarbonate. Similarly, "Boc" refers to t-butoxycarbonyl. The abbreviation "DMAP" refers to 4-dimethylaminopyridine.

The process of this invention is useful for providing compounds of Formula 8, or their enantiomers, which are readily acylated or alkylated to prepare the corresponding compounds of Formula (+)-1a, or their enantiomers (−)-1a. Examples of compounds of Formula 8, or their enantiomers, which may be produced by the process of this invention include the following: (4S,5R)-4,5-diphenyl-3-pyrazolidinone, (4R, 5R)-4,5-diphenyl-3-pyrazolidinone, (4S,5R)-4,5-dinaphthyl-3-pyrazolidinone, (4R,5S)-4,5-dinaphthyl-3-pyrazolidinone, (4S,5R)-4,5-dipyridyl-3-pyrazolidinone, (4R,5S)-4-phenyl-5-methyl-3-pyrazolidinone, (4S,5R)-4-(1-naphthyl)-5-benzyl-3-pyrazolidinone, (4R,5S)-4-phenyl-5-t-butyl-3-pyrazolidinone, (4R,5S)-4-ethyl-5-phenyl-3-pyrazolidinone, ( 4S, 5R) -4-(3-chlorophenyl)-5 -phenyl-3-pyrazolidinone, (4R, 5S)-4-(2-methylphenyl)-5-(2-naphthyl)-3-pyrazolidinone, (4S, 5R)-4-(3-naphthyl)-5-phenyl-3-pyrazolidinone, (4S, 5R)-4-(3-methoxyphenyl)-5-phenyl-3-pyrazolidinone, (4R,5S)-4-(2-chloro-4-methylphenyl)-5-(1-naphthyl)-3-pyrazolidinone, (4S,5R)-4-(3,4-dichlorophenyl)-5(2-fluorophenyl)-3-pyrazolidinone, (4S, 5R) -4-(3-trifluoromethylphenyl)-5-(4-aminophenyl)-3-pyrazolidinone, and (4S, 5R)-4-(4-trifluoromethylphenyl)-5-(3-benzylaminophenyl)-3-pyrazolidinone.

The process provided by this invention is illustrated in Scheme 1. Key aspects of this invention are summarized as follows. First, the epoxide starting materials (2) for this process are readily prepared in enantiomerically pure form by methods known in the art as described below. Second, these epoxides can be converted to hydroxypyazolidinones of formula 4 either directly in one step or by a two step process involving intermediate 3. The hydroxypyrazolidinones thus prepared have clearly defined absolute and relative stereochemical relationships at C-4 and C-5. Third, this-invention provides a method for the selective reduction of hydroxypyrazolidinones 4 to the corresponding pyrazolidinones 8 with complete retention of enantiomeric purity. This involves the activation of the C-O bond by acylation of 4 on N¹ and the OH group to afford 6, selective reductive cleavage to provide the N²-Boc-pyrazolidinone 7, and subsequent Boc removal to afford 8. Finally, compounds of Formula 8 can be acylated or alkylated as described in EPO Publication 467 614 A1 to form the enatiomerically pure derivatives (+)-1a.

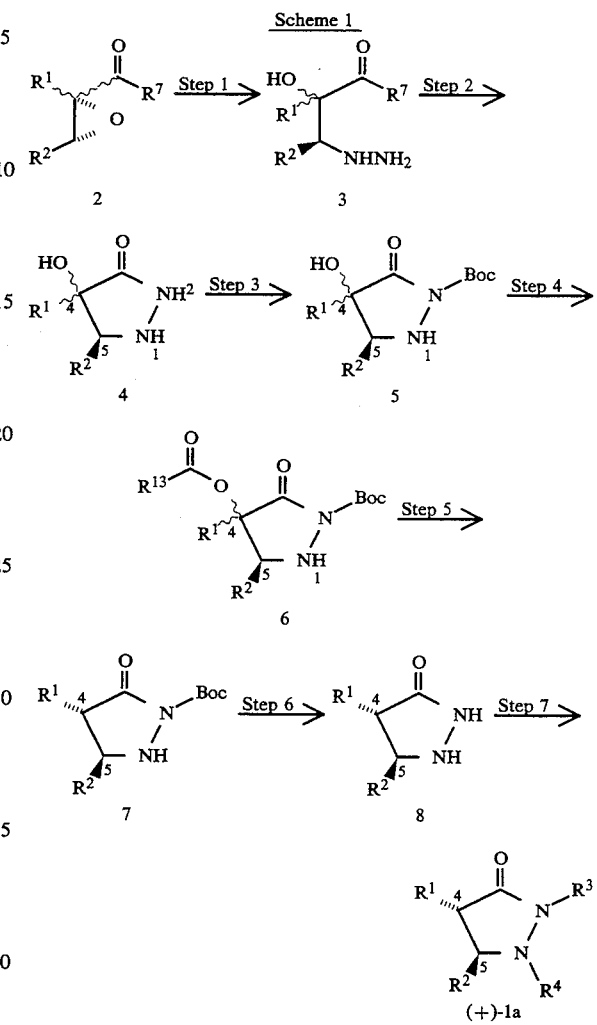

The practitioner will recognize that the antipodal pyrazolidinones of Formula (−)-1a can similarly be prepared by this process from enantiomerically pure epoxides having the opposite absolute configuration to that of 2. The necessary epoxide starting materials for either stereoisomer can be prepared using known chemical methods as described by Gao et al., J, Am. Chem. Soc., 109, 5765–5780 (1987); and Katsuki et al., J. Am. Chem. Soc., 102, 5976–5978 (1980). In those instances where only one absolute configuration is illustrated in the teachings and claims, the scope of the invention is in no way limited by the illustrated absolute stereochemistry.

The key hydroxypyrazolidinone intermediates of Formula 4 are prepared by heating an epoxy compound of Formula 2 with hydrazinc. When the reaction is conducted with the α,β-epoxy acid, 2 (wherein R¹ and R² are cis phenyls, and R⁷ is OH) in refluxing methanol as the solvent the corresponding acyclic β-hydrazino-α-hydroxycarboxylic acid, 3 (where R⁷ is OH), is formed as a major product. One ordinarily skilled in the art will recognize that the regioselectivity of the epoxide opening with hydrazinc (Step 1 of Scheme 1) will be significantly influenced by the identity of the R¹, R², and R⁷ substituents. In certain instances, depending on the nature of $R^1$, $R^2$, and $R^7$, it may be desirable or even necessary to conduct this step in the presence of a Lewis acid catalyst to maximize the yield of the desired β-hydrazino derivative 3. Examples of Lewis acid catalysts that may be beneficial in this step include $BF_3$, $Ti(IV)$ alkoxides, and salts derived from Li(I), Mg(II), Ca(II), and Zn(II). Specific examples of Lewis acids include $Ti(O-i-Pr)_4$, $LiBF_4$, $CaCl_2$, $(CF_3SO_3)_2Mg$, $MgSO_4$, $Zn(BF_4)_2$, and $(CF_3SO_3)_2Zn$. The skilled artisan will recognize that for given $R^1$ and $R^2$ substituents, appropriate $R^7$ groups can be chosen to optimize the result.

The hydrazino acids 3 can be subsequently cyclized to the hydroxypyrazolidinones 4 by simply heating in an appropriate solvent or by treatment with any one of a variety of cyclodehydrating reagents. For example, hydrazino acid 3 can be cyclized to 4 on treatment with thionyl chloride in methanol. Alternatively, when epoxy acid 2 ($R^7=OH$) is treated with hydrazine in water at reflux, the hydroxypyrazolidinone 4 can be formed directly. Furthermore, when $R^1$ and $R^2$ are phenyl, the product 4 is isolated in a high degree of purity by direct crystallization from the aqueous reaction mixture, thereby eliminating the need for additional costly purification procedures such as column chromatography. Absolute stereochemical purity is preserved in the above transformation: enantiomerically pure epoxy acids of Formula 2 afford enantiomerically pure hydroxy pyrazolidinones of Formula 4. Enantiomerically pure hydroxypyrazolidinones of Formula 4 are not known in the art.

A critical transformation in the process illustrated in Scheme 1 (vide supra) is the reductive removal of the C-4 hydroxyl group from the hydroxypyrazolidinones 4 to generate pyrazolidinones 8. A variety of methods are known in the art for the reductive removal of hydroxyl groups (or their derivatives, e.g. esters) located on a carbon α to a carbonyl group. In general, the ease of effecting the deoxygenation of compounds of Formula 4 to afford the desired pyrazolidinones of Formula 8 is dependent on the structure of the $R^1$ and $R^2$ substituents at C-4 and C-5 respectively. The most desirable pyrazolidinones of Formula 1 in terms of their ability to antagonize the effects of CCK are those in which both the $R^1$ and $R^2$ substituents are aryl groups. The preparation of such compounds from precursors of Formula 4 requires the selective reduction of a benzylic C-O bond in the presence of N-N and benzylic C-N bonds, both of which are subject to reductive cleavage under similar conditions. P. Rylander, Catalytic Hydrogenation in Organic Syntheses; Academic Press: New York, (1979).

This invention describes a process for effecting the desired transformation of enantiomerically pure hydroxypyrazolidinones of Formula 4, where $R^1$ and $R^2$ may be aryl groups, to the corresponding enantiomerically pure trans-pyrazolidinones of Formula 8. Since the direct reduction of 4 to 8 proved unsuccessful, a means of activating the C-O bond toward reductive cleavage was required. It was discovered that the necessary activation is achieved by $N^2$, O-bisacylation as follows. On treatment with one equivalent of $Boc_2O$ in the presence of an acyl transfer catalyst, 4 is selectively converted to the $N^2$-Boc derivative 5. Acylation of 5 with one equivalent of a carboxylic anhydride in the presence of an acyl transfer catalyst affords N2,O-bisacylated derivative 6. Alternatively 4 can be converted directly to the $N^2$,O-bis-Boc derivative 6a on treatment with two equivalents of $Boc_2O$ / acyl transfer catalyst. Subsequent reduction of either 6 or 6a affords the $N^2$-Boc pyrazolidinone 7, which is converted to pyrazolidinone 8 on treatment with acid.

The entire process for the conversion of 4 to the desired trans-pryazolidinone of Formula 8 can be effected without isolation or purification of any of the intermediates. Furthermore, the entire reaction sequence is conducted with complete preservation of absolute stereochemical purity. The absolute configuration of the C-5 stereocenter is retained throughout the process, while the absolute configuration of the C-4 stereocenter in 8 and its precursor 7 is controlled by the preference for generating the thermodynamically favored trans diastereomer. Therefore, regardless of the absolute configuration of the C-4 stereocenter in hydroxypyrazolidinone 4, the selective reduction will ultimately provide the same trans-4,5-disubstituted product 8. The practical consequences of this is that two different epoxide diastereomers can serve as precursors to a single trans-pyrazolidinone enantiomer of Formula 8 as depicted in Scheme 2. Thus, in the case of a compound of Formula 4 wherein $R^1$ and $R^2$ are cis phenyl groups, the C-4 hydroxyl group is replaced by hydrogen with clean stereochemical inversion to afford the corresponding transpyrazolidinone 7, which is the same product that would be obtained from the corresponding cis-hydroxypyrazolidinone 4 having the same absolute configuration at C-5.

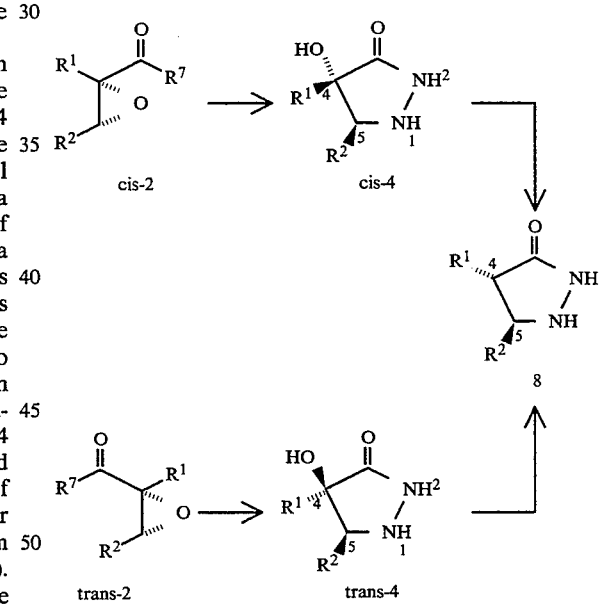

The N,O-bis-Boc-pyrazolidinones (6a) have proven to be ideal substrates for effecting the desired C-O bond cleavage reaction. First, the Boc groups, which activate the $C^4$-O bond toward reductive cleavage, are readily installed as described above in high yield under very mild conditions. Second, the reduction of 6a to 7 can be effected by two alternative and complementary methodologies, thus accommodating a diversity of substituents ($R^1$ and $R^2$) at C-4 and C-5. For the example where $R^1$ and $R^2$ are both phenyl groups, the selective reduction of 6a to 7 has been effected both by dissolving alkali (or alkaline earth) metal reduction (e.g. lithiumammonia) as well as by low-pressure hydrogenation over noble metal catalysts (e.g. 1 atmosphere of $H_2$, Pd on carbon). For the latter method, a dramatic enhancement of $C^4$-O vs $C^5$-N cleavage selectivity as well as reaction rate was observed when the hydrogenation was conducted in the presence of a tertiary amine (e.g. triethylamine). Third, removal of the remaining Boc activating group from 7 can be readily effected in high yield under mild conditions on treatment with non-aqueous acid (e.g. trifluoroacetic acid in methylene chloride or HCl in ethyl acetate), under conditions which the sensitive pyrazolidinone nucleus is not decomposed or racemized.

The formation of the valuable N,O-bis-Boc-pyrazolidinone intermediates of Formula 6a by treatment of hyroxypyrazolidinones 4 with 2 equivalents of $Boc_2O$ in the presence of an acyl transfer catalyst was quite surprising in view of the relevant art. Pyrazolidinones of Formula 1, wherein $R^3$ and $R^4$ are both hydrogen, are known to react with other electrophiles (including other acylating agents) preferentially at the more nucleophilic $N^1$ position: S.D. Perri, et al., *J. Org. Chem.*, 55, 6037–6047 (1990). Similarly, hydroxypyrazolidinone 4, wherein $R^1$ and $R^2$ are phenyt, displayed a high degree of regioselectivity for substitution at $N^1$ on treatment with 4-bromophenylisocyanate. Specifically, following the treatment of 4, wherein $R^1$ and $R^2$ are cis phenyl groups, with 1.1 equiv. of 4-bromophenyl isocyanate at 25° C., the $N^1$-(4-bromophenyl urea) derivative was isolated in 95% yield. In direct contrast, the same hydroxypyrazolidinone 4 afforded the corresponding $N^2$-Boc derivative 5 in 84% yield on treatment with 1.0 equivalent of $Boc_2O$ and 0.08 equiv of DMAP. Furthermore, when compound 4, wherein $R^1$ and $R^2$ are phenyl groups, was treated with 2.2 equivalents of $Boc_2O$ and 0.16 equivalents of DMAP, the corresponding $N^2$,O-bis-Boc derivative 6a was formed in 90% yield. Thus, hydroxypyrazolidinones of Formula 4 were found to react with $Boc_2O$/acyl transfer catalyst with an unusual and totally unexpected regioselectivity in which the relative rates of Boc-substitution at the various positions followed the trend: $N^2 > C^4$-Hydroxyl $> N^1$. The reverse order of reactivity would have been expected based on prior art.

This invention provides a highly enantio-selective process for the preparation of compounds of Formula (+)-1a, (−)-1a, and the corresponding intermediates as claimed herein. The process of this invention provides desired compounds with about 99% enantiomeric excess (ee) or greater when an epoxide of sufficient enantiomeric purity is used. This process is especially advantageous because it is appropriate for large scale equipment. The process may also be appropriate for adaptation to polymer supported reagents. The equipment necessary to carry out the process is of the type commonly found in organic chemical processing plants.

In Scheme 1 and in each of the subsequently described schemes and equations, preferred $R^1$ and $R^2$ are independently selected from the group consisting of phenyl, benzyl, naphthyl, pyridyl and substituted phenyl having 1, 2, or 3 substituents selected from the group consisting of $C_1$–$C_6$ alkyl, $C_1$–$C_6$ alkoxy, $C_1$–$C_6$ alkylthio, chloro, fluoro, trifluoromethyl, phenyl, phenoxy, phenyl($C_1$–$C_4$ alkyl), phenyl($C_1$–$C_4$ alkoxy), cyano, carbamyl, methylenedioxy, amino, —NH($C_1$–$C_4$ alkyl or benzyl ) , and N($C_1$–$C_4$ alkyl)$_2$. More preferredly $R^1$ and $R^2$ are independently selected from the group consisting of phenyl, naphthyl and substituted phenyl (defined supra).

Most preferredly, $R^1$ and $R^2$ are independently phenyl or substituted phenyl having 1 or 2 substituents selected from the group consisting of Cl, F, $C_1$–$C_6$ alkyl, $C_4$–$C_6$ cycloalkyl, $C_1$–$C_6$ alkoxy, phenoxy, and $CF_3$.

Equation 1 illustrates that 4 can be prepared directly from 2 using hydrazine. The solvent for this step may be water or hydrazine-compatible solvents. Examples of hydrazine-compatible solvents include methanol, ethanol, and butanot. A preferred solvent when $R^1$ and $R^2$ are each phenyl is an aqueous solvent ($\geq$95% water). Aqueous solvents having at least 98% water are especially preferred.

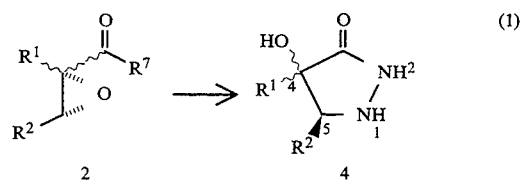

The direct conversion of hydroxypyrazolidinones of Formula 4 to $N^2$,O-bis-Boc derivatives of Formula 6a is illustrated in Equation 2. Most preferably, this step uses about 2 equivalents of $Boc_2O$ in the presence of a catalytic quantity of an acyl transfer catalyst. Appropriate solvents for this step include nonprotic solvents having a high dielectric constant. Furthermore, solvents for this step should be compatible with $Boc_2O$ and the acyl transfer catalyst. Preferred solvents include acetonitrile, ethyl acetate, tetrahydrofuran, and methylene chloride. More preferred solvents include acetonitrile and ethyl acetate.

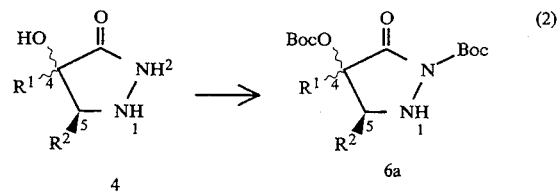

The selective reductive cleavage process illustrated in Scheme 1, Step 5 and Equation 3 can be accomplished using dissolving metal reduction conditions or palladium catalyzed reductive cleavage. Preferredly, the dissolving metal reduction is completed using lithium and ammonia. Most preferredly, the selected reductive cleavage is accomplished using palladium catalyzed reductive cleavage.

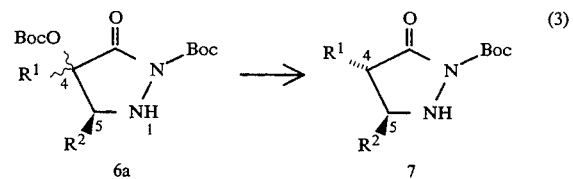

Palladium catalyzed reductive cleavage can be accomplished using palladium catalyst, solvent, and $H_2$. The process may be accomplished under hydrogen pressure ranging from about 0.5 psi to about 50 psi. If desired, the process may be run at elevated temperature (up to about 50° C.). Examples of palladium catalysts include $Pd(OH)_2$, $Pd/BaSO_4$, Lindlar catalyst, and Pd/C. Preferably, there is from about 5% Pd/C to about 20% Pd/C or from about 5% Pd/$BaSO_4$ to about 20% Pd/$BaSO_4$. The most preferred palladium catalyst is about 10% Pd/C. Most preferredly, the process is completed under 1 atmosphere of hydrogen. The process is effective at temperatures from about 0° C. to about 50° C. More preferably, the process is carried out at about 20° C. to about 30° C. Most preferably, the process is completed at about 21° C. to 25° C.

The selective reduction process can be completed using a solvent appropriate for catalytic hydrogenation. Such solvents include alcohols, esters, and hydrocarbons. More preferred solvents include methanol, ethanol, ethyl acetate, acetonitrile, and toluene.

Significantly, the selectivity of the reductive cleavage is enhanced by the presence of a tertiary amine. Preferred tertiary amines include triethylamine, diethylmethylamine, and trimethylamine. Preferably, from about 1 molar equivalent to about 15 molar equivalents of tertiary amine are present. The effect of a tertiary amine on reduction selectivity is illustrated in Table 1.

TABLE 1
Effect of Amines on Reduction Selectivity (eq 4).

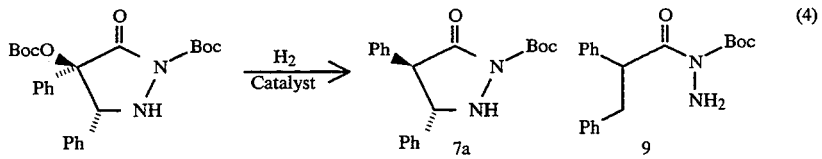

| Catalyst | Additive | Conditions | Ratio of 7a:9[a] | % Isolated Yield of 7a |
|---|---|---|---|---|
| 10% Pd/C | None | 40 psi $H_2$/22° C. 18 h/EtOH; 50° C./5 h | 1:1 | 34 |
| 5% Pd/BaSO$_4$ | None | 1 atm $H_2$/22° C. 19 h/EtOH | 1:12 | (30% rec. starting material) |
| 5% Pd/BaSO$_4$ | Et$_3$N 10 eq. | 1 atm $H_2$/22° C. 14 h/EtOH | >99:1 | 84 |
| 10% Pd/C | Et$_2$NMe 10 eq. | 1 atm $H_2$/22° C. 16 h/EtOH | >99:1 | 90 |
| 10% Pd/C | Et$_3$N 10 eq. | 1 atm $H_2$/22° C. 16 h/CH$_3$CN | >99:1 | 83 |

[a]Ratio of 7a:9 determined by 300 MHz $^1$H NMR spectroscopy.

After selective reductive cleavage, the mixture or isolated product is contacted with an acid to provide compounds of Formula 8 described supra in Scheme 1. Preferably, the selective reductive cleavage product (7) is contacted with a protic acid. If desired, the product of selective reductive cleavage may be subjected to solvent exchange. The most desired solvent is ethyl acetate. Preferred acids include HCl, HBr, HI, trifluoroacetic, and sulfuric. Most preferred acids are anhydrous HCl, HBr, trifluoroacetic. Especially preferred is anhydrous HCl.

The concentration of the reactants for all of the described processes is not critical unless indicated. The artisan can alter the concentration of the reactants to achieve the desired rate of reaction and product yield. In general, the optimum time and temperature for carrying out specific steps of the process will vary with the structure of the substrate. As is always the case in chemistry, the rate of the reaction depends on a variety of factors such as the temperature and the exact compound which is to be prepared. The course of the reaction may be followed using methods such as thin layer chromatography (TLC), high performance liquid chromatography (HPLC), gas chromatography (GC), and nuclear magnetic resonance spectroscopy (NMR) to detect the degree of completion of the reaction. Alternatively, the operator may wish to obtain maximum through put by stopping the reaction at the point at which it reaches an economical degree of completion.

Certain embodiments within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

A) $R^1$ and $R^2$ are independently selected from the group consisting of phenyl, benzyl, naphthyl, pyridyl and substituted phenyl having 1, 2, or 3 substituents selected from the group consisting of $C_1$-$C_6$ alkyl, $C_1$-$C_6$ alkoxy, $C_1$-$C_6$ alkylthio, chloro, trifluoromethyl, phenyl, phenoxy, phenyl ($C_1$-$C_4$ alkyl), phenyl($C_1$-$C_4$ alkoxy), carbamyl, methylenedioxy, $C_3$-$C_6$ alkene, amino, —NH($C_1$-$C_4$ alkyl or benzyl), and N($C_1$-$C_4$ alkyl)$_2$.

B) For the process of Equation 1 when $R^1$ and $R^2$ are each phenyl and $R^7$ is OH the solvent is 95% or more water.

C) For the process of Equation 1 when $R^2$ is phenyl or substituted phenyl, $R^1$ is not hydrogen.

D) In the process of Equation 2 from about 1 mole to about 20 mole % acyl transfer catalyst by weight is present.

E) In the process of Equation 2, from about 2 to about 2.5 equivalents of Boc$_2$O are present.

F) In the process of Equation 2 the solvent is one or more solvents selected from the group consisting of acetonitrile, tetrahydrofuran, methylene chloride, and ethyl acetate.

G) The palladium catalyst is selected from 5–20% Pd/C and Pd/BaSO$_4$.

H) In the process of Scheme 1, Step 5, the solvent is one or more solvents selected from the group consisting of alcohols, acetonitrile, and ethyl acetate.

I) In the process of Scheme 1, Step 5 the selective reductive cleavage is palladium catalyzed hydrogenation.

J) The process of Scheme 1, Step 5 uses $H_2$ under 1 atm of pressure.

K) In the process of Scheme 1, Step 5 a tertiary amine is present in the palladium catalyzed reduction.

L) The acid of Scheme 1, Step 6, is a protic, anhydrous acid.

M) $R^7$ is OH.

N) $R^1$ and $R^2$ are independently selected from the group consisting of phenyl having zero, one, or two substituents independently selected from the group consisting of chloro, $C_1$–$C_6$ alkyl, alkoxy, phenoxy, $CF_3$, and $C_4$–$C_6$ cycloalkyl.

O) In the process of Equation 2 about 5 mole % DMAP is present.

P) In the process of Equation 2 about 2 equivalents of $Boc_2O$ are present.

Q) In the process of Equation 2 the solvent is one or more solvents selected from acetonitrile and ethyl acetate.

R) The palladium catalyst is about 10% Pd/C or about 5% Pd/BaSO$_4$.

S) In the process of Scheme 1, Step 5 the solvent is one or more solvents-selected from the group consisting of ethanol, methanol, acetonitrile, and ethyl acetate.

T) The tertiary amine in the palladium catalyzed reduction is triethylamine or diethylmethylamine.

U) From about 0.5 molar equivalents to about 10 equivalents of tertiary amine is present in Scheme 1, Step 5.

V) The acid of Scheme 1, Step 6 is selected from the group consisting of HCl, HBr, and trifluoroacetic acid.

W) $R^1$ is phenyl.

X) The compound of Formula 1 prepared using processes of this invention is about 99% enatiomeric excess.

Y) $R^{1a}$ and $R^{2a}$ are independently selected from the group consisting of phenyl, naphthyl, and substituted phenyl having 1, 2 or 3 substituents independently selected from the group consisting of $CF_3$, $C_1$–$C_6$ alkyl, $C_1$–$C_6$ alkoxy, $C_1$–$C_6$ alkylthio, chloro, phenyl, and phenyl ($C_1$–$C_4$ alkyl).

Z) $R^{13}$ is tert-butoxy.

The preferred conditions and intermediates for use in the processes of this invention include the features of A–L. More preferred conditions and intermediates for use in the processes of this invention include M–Z.

The following examples are intended to illustrate the instant invention and are not intended to be interpreted as limiting the scope of the invention in any way.

Preparation 1

Preparation of (Z)-2,3-diphenyl-prop-2-en-1-ol

[G44-3FP-180]

Sodium bis-(2-methoxyethoxy)aluminum hydride (70% in toluene) (Vitride®, 536 g, 1.86 mol) was diluted with 850 mL of toluene and the solution was cooled to −10° C. under a nitrogen atmosphere. A 170 g (0.74 mol) sample of Z-2,3-diphenyl propenoic acid was added portionwise to the Vitride solution while maintaining the temperature of the reaction mixture below 10° C. The resulting mixture was stirred at 0°–5° C. until thin layer chromatography indicated total consumption of the carboxylic acid (1.5 hours). A 1.7 L sample of n-butanol was added slowly at about 25° C. until the exotherm and foaming subsided. The speed of addition of the butanol was increased as the exotherm and-foaming stabilized. The pH of the resulting cloudy mixture was adjusted from 11 to 3.5–4.0 with 1.66 L of 3N aqueous HCl. The layers were separated. The organic layer was washed two times with water and dried (Na$_2$SO$_4$). The mixture was filtered and the drying agent was washed with 1:1 n-butanol:toluene (500 mL). The filtrate was evaporated in vacuo to give 170 g of an amber oil which crystallized on the addition of 50 mL of toluene and 510 mL of heptane. The solid precipitate was collected, washed with heptane, and dried to a constant weight under vacuum at 40° C.

Yield: 127.2 g (81% of theory) Melting point: 69°–73° C. $^1$H NMR (300 MHz, CDCl$_3$) δ7.0–7.4 (m, 10H), 6.69 (s, 1H), 4.45 (bs,2H), 1.70 (bs, 1H)

Preparation 2

(2R, 3R)-2,3-cis-Diphenyloxiran-2-yl methanol

[G44-3FP-211]

A reaction vessel was charged with 6.2 g (30 mmol) of diethyl D-tartrate, 12.6 g of powdered, 4 angstrom, activated molecular sieves, and 420 mL of dichloromethane under dry nitrogen. The mixture was cooled to −35° to −30° C. with stirring. Titanium (IV) isopropoxide (5.7 g, 20 mmol) was added and the mixture was stirred at about −25 ° C. for 10–20 min. A 156 mL (20 mmol) sample of t-butyl hydroperoxide (2.6M in isooctane) was added slowly to the reaction mixture maintaining the temperature at less than −20° C. The mixture was stirred at −35° to −20° C. for about 35 minutes. A solution of the product of Preparation 1 (42.1 g, 200 mmol) in 210 mL of dichloromethane was added to the reaction mixture slowly, keeping the temperature at less than −20° C. The mixture was stirred for 1.5 h at −25° to −20° C. at which point HPLC analysis (vide infra) indicated the reaction was complete. The mixture was warmed to 0° C. and quenched by the addition of 115 mL of water. The remaining diethyl D-tartrate was hydrolyzed by the slow addition at 18° C. of 24 mL of an aqueous sodium hydroxide solution (prepared by dissolving sodium hydroxide (600 g) and sodium chloride (100 g) in 1.8 L of water). After stirring at 25° C. for about 30 min, 45 mL of methanol was added and the lower organic layer was separated. The aqueous layer was extracted with dichloromethane (170 mL). The organic layers were combined, dried (MgSO$_4$), and evaporated to give 47.3 g of an off-white solid which was recrystallized from toluene (70 mL) and heptane (190 mL) to afford the title compound as a white crystalline solid.

Yield: 32.3 g (71% of theory) Melting Point: 87°–91° C. Purity by HPLC: 99.2% (HPLC conditions for the purity assay: 4.6 mm × 15 cm Zorbax ® RX-C8 column; acetonitrile:0.1% aqueus H$_3$PO$_4$ eluent; 2mL/min; uv detection at 225 nm) Chiral HPLC assay: >99% ee (HPLC conditions for the chiral assay: 4.6 mm × 25 cm Chiralcel® OJ column; 40° C.; 85:15 hexane:1-propanol eluent; 1 mL/min; uv detection at 258 nm; The (2R,3R)-enantiomer elutes at 7.4 min; the (2S,3S)-enantiomer elutes at 10.6 min.)

Preparation 3

(2S,3R)-cis-2,3-diphenyloxiranecarboxlic acid

[G44-3FP-243]

To a mixture of 45.3 g, 200 mmol of (2R,3R)-cis-2,3-diphenyloxiran-2-yl methanol (Preparation 2), 180 mL of ethyl acetate, 180 mL of acetonitrile, 362 mL of water, and 902 mg (4.00 mmol) of ruthenium trichloride hydrate, stirred at 25° C. under nitrogen, was added 115 g, (500 mmol) of solid periodic acid. The reaction mixture exothermed to 55° C. and then was cooled to 30° C. for 45 min. The phases were separated and the aqueous layer was extracted with two 135-mL portions of ethyl acetate. Water (180 ml) was added to the combined organic phases and the pH was adjusted to 9.5 by the dropwise addition of aqueous sodium hydroxide with stirring. After separation of the phases, the organic phase was again subjected to the above aqueous extraction procedure. The aqueous extracts were combined and washed successively with ethyl acetate (190 mL), dichloromethane (190 mL), and t-butyl methyl ether (40 mL). The aqueous phase was adjusted to pH 2.5 with HCl, and was then extracted with two 180-mL portions of dichloromethane. The dichloromethane extracts were combined, dried ($Na_2SO_4$), and evaporated in vacuo to give 38.2 g of dark solid. The solid was stirred with 40 mL of t-butyl methyl ether for 30 min and then heptane (570 ml) was added in a slow stream at room temperature. The mixture was cooled to 0° C. and the precipitate was collected, washed with heptane, and dried to constant weight at 25° C./3 mm of Hg:

Yield: 31.2 g (65% of theory) Melting Point: 104°–108° C. Purity by HPLC (as described in Preparation 2): >99% Chiral HPLC assay: >99% ee (HPLC conditions for the chiral assay: The assay was performed on the methyl ester prepared by reacting the sample with diazomethane. 4.6 mm×25 cm Chiralcel® OD column; 40° C.; 85:15 hexane:1-propanol eluent; 1 mL/min; uv detection at 228 nm; the 2S,3R enantiomer elutes at 5.8 min; the 2R,3S enantiomer elutes at 4.3 min.) $^1H$ NMR (300 MHz, DMSO-$d_6$) δ10.71 (s, 1H), 7.00–7.31 (m, 10H), 4.60 (s, 1H).

EXAMPLE 1

(4S,5S)-4-Hydroxy-cis-4,5-diphenyl-3-pyrazolidinone

[G44-3FP-283]

A mixture of 480 g (2.00 mol) of (2S, 3R) -cis-2,3diphenyloxirane carboxylic acid (Preparation 3), 1.2 L of n-butanol and 128 mL (131 g, 4.00 mol) of 98% hydrazine was stirred and refluxed under $N_2$ for 2 h. The solution was diluted with 2.2 L of n-butanol and cooled to about 5° C. The precipitate was collected, washed with 1.5 L of cold n-butanol, washed with heptane, and then dried at 40° C. in vacuo to provide the product as a white crystalline solid:

Yield: 288 g (57% of theory) Purity by HPLC (as in Preparation 2): 85% Chiral HPLC assay: >99% ee (HPLC conditions for the chiral assay: 4.6 mm×25 cm Chiralcel® OJ column; 40° C.; 85:15 hexane:1-propanol eluent; 1 mL/min; uv detection at 250 nm. The 4S,5S enantiomer elutes at 10.4 min; the 4R,5R enantiomer elutes at 12.4 min.)

Purification procedure:[G44-3FP-291]Crude (4S,5S)-4-Hydroxy-cis-4,5-diphenyl-3-pyrazolidinone (1070 g) prepared as described above was slurried in 5.4 L of n-butanol and heated to 95° C. The hot mixture was filtered and the solid was washed with 1 L of hot n-butanol. The filtrate was cooled to about 5° C., and the resulting precipitate was collected, washed successively with cold n-butanol (1.5 L), heptane (2 L), and acetonitrile (1.6 L) and then dried under vacuum at 40° C. to afford the purified product as a white solid:

Yield: 639.5 g (60% recovery) Purity by HPLC: 96% Chiral HPLC assay: >99% ee $^1H$ NMR (300 MHz DMSO-$d_6$), δ9.90 (s, 1H), 6.90–7.10 (m, 10H), 6.25 (s, 1H), 5.70 (d, J=11 Hz, 1H), 4.60 (d, J=11 Hz, 1H)

EXAMPLE 2

(4S,5S)-4-Hydroxy-cis-4,5-diphenyl-3-pyrazolidinone

[G44.-6YL-20]

A mixture of 240 g (1.00 mol) of (2S,3R)-2,3-cisdiphenyloxirane carboxylic acid (Preparation 3), 1.2 L of water, and 128 mL (131 g, 4.00 mol) of 98% hydrazine was stirred and refluxed under nitrogen for 17 h. The precipitate that formed on cooling to 25° C. was collected, washed with 720 mL of water, and dried at 40° C./3 mm of Hg to provide the title compound as a white solid:

Yield: 181.1 g (71.2% of theory Melting Point: 184°–87° C. Purity by HPLC: >99% Chiral HPLC assay: >99% ee $^1H$ NMR as reported in Example 1.

EXAMPLE 3

(4S, 5S)-$N^2,O^4$-bis-Boc-4-Hydroxy-cis-4,5-diphenyl-3-pyrazolidinone and (4S, 5S)-$N^1,N^2,O^4$-tris-Boc-4-Hydroxy-cis-4,5-diphenyl-3-pyrazolidinone

[M43-7YR-228]

To a mixture of 25.6 g (0.100 mol) of (4S,5S)-4-hydroxy-4,5-cis-diphenyl-3-pyrazolidinone, 610 mg (5.0 mmol) of 4-dimethylaminopyridine (DMAP), and 250 mL of dry acetonitrile, stirred at 25° C. under $N_2$, was added a solution of 48.6 g (222 mmol) of di-t-butyl dicarbonate in 20 mL acetonitrile dropwise over a 15 min period. The resulting solution was stirred for 1 h at room temperature. HPLC analysis (vide infra) indicated that the solution consisted of a 92:8 mixture of the $N^2,O$-bis-Boc and $N^1,N^2,O^4$-tris-Boc derivatives, respectively, of the starting hydroxypyrazolidinone.

EXAMPLE 4

(4S,5R)-trans-4,5-diphenyl-3-pyrazolidinone

To the above solution (Example 3) was added 22.9 g of 10% Pd on C, 150 mL of acetonitrile, and 122 mL (87.8 g, 1.00 mol) of N,N-diethylmethylamine. The reaction mixture was stirred under 1 atm of $H_2$ at 20°–25° C. for 9 h and then filtered through diatomaceous earth filter aid to remove the catalyst. The filter cake was washed with three 100-mL portions of acetonitrile and the filtrate was evaporated in vacuo. Residual N,N-diethylmethylamine was removed by the addition, and subsequent evaporation in vacuo of two 250-mL portions of ethyl acetate. The residual white foam was dissolved in 350 mL of ethyl acetate and filtered to remove a small amount of precipitate. The filtrate was purged with $N_2$, cooled to 5° C., and stirred while a total of 31 g of anhydrous HCl gas was introduced via a sintered-glass gas diffusion tube over a 30 min period. Following HCl addition, the reaction mixture was stirred under $N_2$ for 5 h at 25° C. during which time a white precipitate formed. The precipitate was collected, washed with three 30-mL portions of ethyl acetate, and dried at 25° C./3 mm of Hg for 17 h to yield 19.51 g of (4S,5R)-trans-4,5-diphenyl-3-pyrazolidinone hydrochloride as a white solid.

The above solid was added to a stirred mixture of dichloromethane (200 mL) and pH 7 aqueous phosphate buffer (200 mL) under $N_2$. Within 15 min the solid dissolved and the phases were separated. The aqueous phase was extracted with four 50-mL portions of dichloromethane. The organic extracts were combined, dried (Na$_2$SO$_4$), and evaporated in vacuo to yield a white foam which crystallized on trituration with ethyl acetate. Residual solvent was evaporated in vacuo and the remaining solid was dried at 25° C./3 mm of Hg for 72 h to afford the title compound as a white crystalline solid:

Yield: 16.1 g (67% of theory) Melting Point: 144.5°–146.5° C. Purity by HPLC (as in preparation 2): 95% Chiral HPLC assay: >99% (HPLC conditions for the chiral assay: 4.6 mm×25 cm Chiralcel® OD column; 40° C.; 80:20 hexane:1-propanol eluent; 1.5 mL/min; uv detection at 250 nm. The 4S,5R enantiomer elutes at 7.0 min; the 4R,5S enantiomer elutes at 9.0 min.) $^1$H NMR (CDCl$_3$, 300 MHz) δ7.47 (bs, 1H), 7.23–7.38 (m, 10H), 4.79 (t, J=10.7 Hz, 1H), 4.36 (d, J=10.7 Hz, 1H), 4.00 (d, J=10.6 Hz, 1H).

EXAMPLE 5

Synthesis of (4S, 5R)-trans-4,5-Diphenyl-3-Pyrazolidinone

[M43-9YL-136]

To a mixture of 10.16 g (40.0 mmol) of (4S,5R)-4-hydroxy-trans-4,5-diphenyl-3-pyrazolidinone, 0.24 g (2.0 mmol) of DMAP, and 60 mL of ethyl acetate, stirred at 25° C. under nitrogen, was added a solution of 21.8 g (0.100 mol) of di-t-butyl dicarbonate in 40 mL of ethyl acetate over a 10 min period.

After stirring at 25° C. for one hour, the above solution was treated with 9.08 g of 10% Pd on C, 11 mL (91 mmol) of N,N-diethylmethylamine and 10 mL of ethyl acetate. The resulting mixture was stirred at 20°–25° C. under 1 atm of hydrogen for 23 h at which time HPLC indicated the reductive cleavage to be about 85% complete. An additional 4.5 g of 10% palladium on carbon and 25 mL of ethyl acetate was introduced and the reaction mixture was stirred under 1 atm of H$_2$ for an additional 22 h. The catalyst was removed by filtration through diatomaceous earth and the filter cake was washed with three 30-mL portions of ethyl acetate. The filtrate was concentrated to about one-half the original volume in vacuo and then diluted back to 100 mL total volume with ethyl acetate. This solution was placed under a nitrogen atmosphere and cooled to 5° C. A total of 24.3 g of anhydrous HCl gas was introduced into the solution over a 5 min period and the resulting mixture was stirred at 25° C. under N$_2$ for 19 h, during which time the (4S,5R)-4,5-diphenyl-3-pyrazolidinone hydrochloride separated as a white precipitate. The precipitate was collected, washed with three 20-mL portions of ethyl acetate, and added to a mixture of dichloromethane (100 mL) and pH 7 aqueous phosphate buffer (100 mL). The mixture was stirred for 10 minutes under nitrogen and the phases were separated. The aqueous phase was extracted with 50 mL of dichloromethane. The organic phases were combined, filtered to remove a small amount of fine precipitate, and concentrated to 30 mL by distillation under 1 atm of N$_2$. Toluene (120 mL) was added and distillation continued until the vapor temperature of the distillate reached 109° C. The residue was cooled to 0° C. and the resulting precipitate was collected, washed with cold toluene, and dried at 50° C./3 mm of Hg for 18 h to provide (4S,5R)-trans-4,5-diphenyl-3-pyrazolidinone as a white solid:

Yield: 6.78 g (71% of theory) Melting Point: 144.5°–145.5° C. Elemental Analysis C$_{15}$H$_{14}$N$_2$O: Calculated: C, 75.61; H, 5.92; N, 11.76 Found : C, 75.88; H, 5.86; N, 11.96 Specific Rotation: [α]$_D$= −129° (CHCl$_3$, c=0.01). Chiral HPLC assay (vide supra): >99% ee $^1$H NMR as reported in Example 5.

EXAMPLE 6

(+)-(4S,5R)-N-(4-bromophenyl)-3-oxo-trans-4,5-diphenyl-1-pyrazolidinecarboxamide

[M43-7YR-235]

To a solution of 15.6 g (65 mmol) of (4S,5R)-trans-4,5-diphenyl-3-pyrazolidinone (Example 4) in 120 mL of dichloromethane, stirred at −10° C. under dry nitrogen, was added a solution of 12.8 g (65 mmol) of 4-bromophenyl isocyanate in 20 mL of dichloromethane dropwise over a 15 min period. The mixture was stirred for 1 h at −5° C. and then filtered to remove a small amount of 1,3-bis(4-bromophenyl)urea. The dichloromethane was evaporated in vacuo and the resulting white foam crystallized on addition of 250 mL of toluene:heptane (90:10). The precipitate was collected, washed with three 35-mL portions of toluene:heptane 90:10, washed with 50 mL of heptane, and vacuum dried at 50° C./3 mm of Hg for 40 hours to yield 23.9 g of the title compound as a white solid:

Yield: 23.89 g (84% of theory) Melting Point: 110°–113° C. Purity by HPLC (as in Preparation 2): 97% Chiral HPLC assay: >99% ee (HPLC conditions for the chiral assay: 4.6 mm×25 cm Chiralpak® AD column; 40° C.; 70:30 hexane:ethanol eluent; 1.5 mL/min; uv detection at 250 nm. The 4S,5R enantiomer elutes at 9.7 min; the 4R,5S enantiomer elutes at 7.1 min.) Specific Rotation: [α]$_D$=46.6° (CHCl$_3$, c=0.01) Elemental analysis C$_{22}$H$_{18}$BrN$_3$O$_2$: Calculated: C, 60.56; H, 4.16; N, 9.63; Br, 18.31 Found: C, 60.38; H, 4.11; N, 9.64; Br, 18.12

EXAMPLE 7

(+)-(4S,5R)-N-(4-bromophenyl)-3-oxo-trans-4,5-diphenyl-1-pyrazolidine carboxamide

[M43-9YL-123]

To a slurry of 2.00 g (8.40 mmol) of (4S,5R)-trans-4,5-diphenyl-3-pyrazolidinone (Example 4) in 40 mL of toluene, vigorously stirred at 18° C. under N$_2$ in a Morton flask, was added a solution of 1.82 g (8.40 mmol) of 4-bromophenyl isocyanate in 10 mL of toluene over a 2 min period. The starting material dissolved and after 5 min a thick slurry formed. The mixture was stirred for 1 h at 25° C. The precipitate was collected, washed with toluene and vacuum dried at 50° C./3 mm of Hg for 24 h to afford the title compound as a white solid:

Yield: 3.04 g (83% of theory) Purity by HPLC (as in Preparation 2): >99%

EXAMPLE 8

(4R, 5R)-4-Hydroxy-cis-4,5-diphenyl-3-pyrazolidinone

[V95-2FM-133]

A solution of 500 mg (2.08 mmol) of (2R,3S)-cis-2,3-diphenyloxiranecarboxylic acid and 653 μL (20.8 mmol) of 98% hydrazine in 2.5 mL of anhydrous methanol was stirred and refluxed under N$_2$ for 3.5 h. The mixture was diluted with 5 mL of toluene and evaporated in vacuo to afford 506 mg of an off-white foam, shown by 300 MHz $^1$H NMR and HPLC to consist mainly of a 92:8 mixture of the desired β-hydrazino-α-hydroxy acid and the starting α,β-epoxy acid, respectively.

To a mixture of the above foam and 10 mL of anhydrous methanol, stirred at 0° C. under N$_2$, was added dropwise 303 μL (4.16 mmol) of thionyl chloride. The resulting mixture was stirred at 0°-5° C. for 20 min and was then refluxed for 2.5 h. The mixture was cooled to 25° C. and partitioned between 20 mL of 1N pH 7 phosphate buffer and 20 mL of dichloromethane. The aqueous phase was extracted with five 6-mL portions of dichloromethane. The organic phases were combined, dried (Na$_2$SO$_4$), and evaporated in vacuo. The residual yellow foam (501 mg) was chromatographed on a column of 30 g of silica gel (230–400 mesh) eluting with 3:1 ethyl acetate-dichloromethane to yield 270 mg (51% of theory) of the title compound as a white solid.

EXAMPLE 9

(4R,5R)-N$^2$-Boc-4-Hydroxy-cis-4,5-Diphenyl-3-Pyrazolidinone

[V76-7BM-292]

To a mixture of 127 mg (0.50 mmol) of (4R,5R)-4-hydroxy-cis-4,5-diphenyl-3-pyrazolidinone (Example 8), 5 mg (0.04 mmol) of DMAP, and 1 mL of anhydrous acetonitrile, stirred at 25° C. under dry N$_2$, was added 0.11 mL (110 mg, 0.50 mmol) of di-t-butyl dicarbonate (>97%) portionwise over a 1.5 h period. The resulting solution was stirred at 25° C. for 1 h additional, and was then evaporated in vacuo. The residue was chromatographed on a column of 40 g of silica gel (230–400 mesh) eluting with 83:17 hexane-ethyl acetate (300 mL) followed by 80:20 heaxane-ethyl acetate to yield 149 mg (84%) of the title compound as a white solid:

$^1$H NMR (300 MHz, CDCl$_3$) δ7.19-7.05 (m, 6H, aromatics), 6.99-6.95 (m, 2H, aromatics), 6.91-6.88 (m, 2H, aromatics), 5.25 (d, J=9.9 Hz, 1H, N$^1$-H), 4.80 (d, J=9.9 Hz, 1H, C$^5$-H), 3.74 (s, 1H, OH), 1.62 (s, 9H, C(CH$_3$)$_3$);

$^{13}$C NMR (75.5 MHz, CDCl$_3$) δ172.0, 148.1, 135.7, 133.1, 128.3, 128.1, 127.9, 127.8, 127.0, 126.0, 85.1, 82.2, 69.0, 28.0.

EXAMPLE 10

(4R,5R)-N$^2$,O$^4$-Bis-Boc-4-Hydroxy-cis-4,5-Diphenyl-3-Pyrazolidinone

[V76-7BM-298]

To a mixture of 1.017 g of (4R,5R)-4-hydroxy-cis-4,5-diphenyl-3-pyrazolidinone (Example 8), 40 mg (0.33 mmol) of DMAP, and 8.0 mL of acetonitrile, stirred at 25° C. under N$_2$, was added 1.80 mL (1.81 g, 8.29 mmol) of di-t-butyl dicarbonate. The resulting solution was stirred at 25° C. for 3.5 hours at which time thin layer chromatography indicated that some N$^2$-mono-Boc substituted material was present. An additional 0.15 mL (0.15 g, 0.69 mmol) of di-t-butyl dicarbonate was added and resulting solution was stirred overnight (12 h) at 25° C. The reaction mixture was partitioned between dichloromethane and pH 7 phosphate buffer. The aqueous phase was extracted with three portions of dichloromethane and the organic phases were combined, dried (Na$_2$SO$_4$), and evaporated in vacuo. The residue was chromatographed on 240 g of silica gel (230–400 mesh) eluting with hexane:ethyl acetate (85:15) to yield 1.56 g of the title compound as a white solid:

Yield: 1.56 g (86% of theory) $^1$H NMR (300 MHz, CDCl$_3$) δ7.20-7.10 (m, 6H, aromatics), 7.01-6.99 (m, 2H, aromatics), 6.87-6.85 (m,2H, aromatics), 5.58 (d, J=9.9 Hz, 1H, CH—N), 5.21 (d, J=9.9 Hz, 1H, NH), 1.64 (s, 9H, C(CH$_3$)$_3$), 1.55 (s, 9H, C(CH$_3$)$_3$). $^{13}$C NMR (75.5 MHz, CDCl$_3$) δ166.8, 151.3,148.1, 133.2, 132.5, 128.6, 128.3,128.0, 127.9, 127.2, 126.3, 87.3, 84.9, 84.0, 63.9, 28.1, 27.7.

EXAMPLE 11

Palladium Catalyzed Reductive Cleavage

[M43-7YR-163]

A mixture of 157 mg (0.34 mmol) of (4R,5R)-N$^2$,O$^4$-bis-Boc-4-hydroxy-cis-4,5-diphenyl-3-pyrazolinone (Example 10) 70 mg of 5% Pd/BaSO$_4$, 4 mL of 2B3 absolute ethanol, and 480 μL (3.4 mmol) of triethylamine was stirred under 1 atm of H$_2$ at 25° C. for 14 h. The catalyst was removed by filtration through diatomaceous earth and the filter cake was washed with five 3-mL portions of absolute ethanol. The filtrate was evaporated in vacuo and the residual white foam (129 mg) was chromatographed on silica gel (230–400 mesh) eluting with 4:1 hexane-ethyl acetate (200 mL) followed by 2:1 hexane-ethyl acetate to provide (4R,5S) -N$^2$-Boc-trans-4,5-diphenyl-3-pyrazolidinone as a colorless, viscous oil:

Yield: 99 mg (84% of theory) Chiral HPLC assay: >99% ee (HPLC conditions for the chiral assay: 4.6 mm×25 cm Chiralcel® OJ column; 40° C.; 85:15 hexane:1-propanol eluent; 1.0 mL/min; uv detection at 250 nm. The 4S,5R enantiomer elutes at 13.0 min; the 4R,5S enantiomer elutes at 10.0 min.) $^1$H NMR (300 MHz, CDCl$_3$) δ7.15-7.38 (m, 10H), 5.00 (d, J=10.0 Hz, 1H), 4.71 (dd, J=10.1 Hz, 11.6 Hz, 1H), 4.05 (d, J =11.6 Hz, 1H), 1.58 (s, 9H).

EXAMPLE 12

Palladium Catalyzed Reductive Cleavage

[M43 -7YR-168]

A mixture of 160 mg (0.35 mmol) of (4R,5R)-N$^2$,O$^4$-bis-Boc-4-hydroxy-cis-4,5-diphenyl-3-pyrazolidinone (Example 10) 40 mg of 10% Pd/C, 4 mL of 2B3 absolute ethanol, and 425 μL (3.5 mmol) of N,N-diethylmethylamine was stirred under 1 atm of H$_2$ at 25° C. for 16 h. The catalyst was removed by filtration through diatomaceous earth and the filter cake was washed with five 3-mL portions of absolute ethanol. The filtrate was evaporated in vacuo and the residual white foam (115 mg) was chomatographed on silica gel (230–400 mesh) eluting with 3:1 hexane-ethyl acetate to provide (4R,5S)-N$^2$-Boc-trans-4,5-diphenyl-3-pyrazolidinone as a white foam:

Yield: 108 mg (90% of theory) $^1$H NMR (300 MHz, CDCl$_3$) δ7.15-7.38 (m, 10H), 5.00 (d, J=10.0 Hz, 1H), 4.71 (dd, J=10.1 Hz, 11.6 Hz, 1H), 4.05 (d, J =11.6 Hz, 1H), 1.58 (s, 9H). Elemental analysis C$_{20}$H$_{22}$N$_2$O$_3$: Calculated: C, 70.99; H, 6.55; N, 8.28 Found: C, 70.46; H, 6.82; N, 7.89 Mass spectrum (Field Desorption): parent peak at m/e 338

EXAMPLE 13

Palladium Catalyzed Reductive Cleavage

A mixture of 50 mg (0.11 mmol) of (4R,5R)-N$^2$O$^4$-bis-Boc-4-hydroxy-cis-4,5-diphenyl-3-pyrazolidinone (Example 10), 20 mg of 10% Pd/C, 2 mL of 2B3 absolute ethanol and 150 μL (1.1 mmol) of triethylamine was stirred under 1 atm of hydrogen at 20°-25° C. for 15 h. Thin layer chromatography (silica gel; 2:1 hexane-ethyl acetate) showed no starting material present. The catalyst was removed by filtration through diatomaceous earth and the filter cake was washed with three 5-mL portions of absolute ethanol. The filtrate was evaporated in vacuo to afford 29 mg of an oil shown by 300 MHz $^1$H NMR to be the desired (4R,5S)-N$^2$-Boc-trans-4,5-diphenyl-3-pyrazolidinone.

EXAMPLE 14

Palladium Catalyzed Reductive Cleavage Without Added Amine

A glass pressure vessel equipped with a magnetic stirring bar was charged with 200 mg (0.44 mmol) of (4R,5R)-N$^2$, O$^4$-bis-Boc-4-hydroxy-cis-4,5-diphenyl-3-pyrazolidinone (Example 10) and 100 mg 10% Pd/C. The vessel was flushed with nitrogen and 4 mL of 2B3 absolute ethanol was added. The reaction mixture was stirred under 40 psi of H$_2$ at 20°–25° C. After 2 h, thin layer chromatography (as in Example 13) indicated the presence of some of the desired (4R,5S)-N$^2$-Boc-trans-4,5-diphenyl-3-pyrazolidinone product. The mixture was stirred for an additional 18 h at which time thin layer chromatography indicated starting material was still present.

The mixture was heated to 50° C. under 40 psi hydrogen. After 5 h the reaction mixture was cooled and the catalyst was removed by filtration through diatomaceous earth. The filter cake was washed with 20 mL of absolute ethanol and the filtrate was evaporated in vacuo. The residual gray foam (150 mg) was chromatographed on 30 g of silica gel (230–400 mesh) eluting with 4:1 hexane-ethyl acetate. Fractions 11–17 (10 mL each) on evaporation in vacuo afforded 51 mg of an oil found to be hydrazide 9 by $^1$H NMR and mass spectroscopy (vide infra). Fractions 21–30 were combined and evaporated in vacuo to give 51 mg the desired product, (4R,5S)-N$^2$-Boc-trans-4,5-diphenyl-3-pyrazolidinone.

Yield of Desired Product: 51 mg (34% of theory)
Yield of Over-reduced Product (Formula 9): 51 mg (34% of theory)

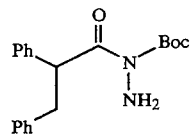

9

$^1$H NMR (300 MHz, CDCl$_3$) δ7.05–7.15 (m, 10H), 5.19 (t, J=7.3 Hz, 1H), 4.25 (m, 2H), 3.45 (dd, J=13.6, 7.5 Hz, 1H), 3.00 (dd, J=13.6, 7.5 Hz, 1H), 1.46 (s, 9H).

EXAMPLE 15

Palladium Catalyzed Reductive Cleavage Without Added Amine

A mixture of 25 mg of (4R,5R)-N$^2$,O$^4$-bis-Boc-4-hydroxy-cis-4,5-diphenyl-3-pyrazolidinone (Example 10), 40 mg of 20% Pd(OH)$_2$ on C, and 2 mL of 2B3 absolute ethanol was stirred at 20°–25° C. under 1 atm of hydrogen for 18 h. Thin layer chromatography (as in Example 13) indicated that the starting material had been consumed. The catalyst was removed by filtration through diatomaceous earth and the filter cake was washed with 15 mL of absolute ethanol. The filtrate was evaporated in vacuo. A solution of the residue in CDCl$_3$ was chromatographed on a short column of alumina to afford 9 mg of an oil shown by 300 MHz $^1$H NMR to be the undesired overreduced product, hydrazide 9.

EXAMPLE 16

Palladium Catalyzed Reductive Cleavage Without Added Amine

[M43 -7YR-159]

A mixture of 25 mg of (4R,5R)-N$^2$,O$^4$-bis-Boc-4-hydroxy-cis-4,5-diphenyl-3-pyrazolidinone (Example 10), 20 mg of 5% Pd on BASO$_4$, and 2 mL of 2B3 absolute ethanol was stirred at 20°–25° C. under 1 atm of hydrogen for 19 h. The catalyst was removed by filtration though diatomaceous earth and the filter cake was washed with 15 mL of absolute ethanol. The filtrate was evaporated in vacuo to yield an oil shown by 300 MHz $^1$H NMR to consist of a 60:35:5 mixture of hydrazide 9, starting material, and desired (4R,5S)-N$^2$-Boc-trans-4,5-diphenyl-3-pyrazolidinone, respectively.

EXAMPLE 17

Dissolving Metal Reduction

[V76-7BM-294]

To 3 mL of anhydrous ammonia, stirred at −78° C. under dry N$_2$, was added 47 mg (0.10 mmol) of (4R,5R)-N$^2$,O$^4$-bis-Boc-4-hydroxy-cis-4, 5-diphenyl-3-pyrazolidinone (Example 10). Anhydrous tetrahydrofuran (2 mL) was added slowly via syringe and after the temperature stabilized at −78° C., 2 mg (0.3 g-atom) of lithium metal (99.9%) was added with stirring. The solution was stirred at −50° to −60° C. for about 10 minutes during which time all the lithium dissolved. The resulting orange solution was quenched by the addition of an excess of solid NH$_4$Cl. The resulting mixture was cautiously added to a large volume of aqueous pH 7 phosphate buffer. The pH was adjusted to 7 by the addition of 2N aqueous H$_2$SO$_4$, and the mixture was extracted with four portions of dichloromethane. The organic extracts were combined, dried(Na$_2$SO$_4$), and evaporated in vacuo. The residue was chromatographed on a column of 10 g of silica .gel (230–400 mesh) eluting with 80:20 hexane-ethyl acetate to afford 13.3 mg of colorless oil found by 300 MHz $^1$H NMR to consist mainly of (4R,5S)-N$^2$-Boc-trans-4,5-diphenyl-3-pyrazolidinone.

The above product was dissolved in 0.5 mL of dichloromethane under N$_2$ and treated with 0.5 mL of trifluoroacetic acid. After stirring for 30 min at 25° C. the solution was diluted with toluene and evaporated in vacuo. The residue was partitioned between dichloromethane and pH 7 phosphate buffer and the aqueous phase was extracted with two portions of dichloromethane. The oragnic extracts were combined, dried (Na$_2$SO$_4$), and evaporated in vacuo. The major product, isolated by silica gel chromatography, was found by 300 MHz $^1$H NMR and chiral HPLC analysis (Example 4) to be (4R,5S)-trans-4,5-diphenyl-3-pyrazolidinone having an enantiomeric purity of at least 97% ee.

We claim:

1. A compound of Formula 4a

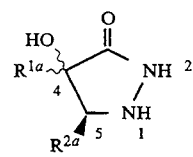

4a wherein R$^{1a}$ and R$^{2a}$ are independently hydrogen, C$_1$–C$_6$ alkyl, phenyl, benzyl, naphthyl, pyridyl or substituted phenyl having 1, 2, or 3 substituents selected from the group consisting of $C_1$–$C_6$ alkyl, $C_1$–$C_6$ alkoxy, $C_1$–$C_6$ alkylthio, chloro, fluoro, trifluoromethyl, phenyl, phenoxy, phenyl($C_1$–$C_4$ alkyl), phenyl($C_1$–$C_4$ alkoxy), cyano, carbamyl, methylenedioxy, $C_3$–$C_6$ alkene, amino, —NH(-$C_1$–$C_4$ alkyl or benzyl), and N($C_1$–$C_4$ alkyl)$_2$; and provided that when $R^{2a}$ is phenyl or substituted phenyl, $R^{1a}$ may not be hydrogen or $C_1$–$C_6$ alkyl and further provided that $R^{1a}$ and $R^{2a}$ may not simultaneously be hydrogen.

2. A compound claim 1 wherein $R^{1a}$ is phenyl or substituted phenyl having 1, 2, or 3 substituents selected from the group consisting of $C_1$–$C_6$ alkyl, $C_1$–$C_6$ alkoxy, $C_1$–$C_6$ alkylthio, chloro, fluoro, trifluoromethyl, phenyl, phenoxy, phenyl ($C_1$–$C_4$ alkyl), phenyl($C_1$–$C_4$ alkoxy), cyano, carbamyl, methylenedioxy, $C_3$–$C_6$ alkene, amino, —NH($C_1$–$C_4$ alkyl or benzyl), and N($C_1$–$C_4$ alkyl)$_2$.

* * * * *

UNITED STATES PATENT AND TRADEMARK OFFICE
CERTIFICATE OF CORRECTION

PATENT NO. : 5,399,708

DATED : March 21, 1995

INVENTOR(S) : William B. Blanchard, et al.

It is certified that error appears in the above-indentified patent and that said Letters Patent is hereby corrected as shown below:

Column 5, line 45, "cyctopropyl" should read, -- cyclopropyl --.

Column 12, line 8, "($\not\geq$ 95% water)" should read, -- ($\geq$ 95% water) --.

Signed and Sealed this

Twenty-first Day of November, 1995

Attest:

BRUCE LEHMAN

Attesting Officer  Commissioner of Patents and Trademarks